(12) United States Patent
Herron et al.

(10) Patent No.: US 7,912,529 B2
(45) Date of Patent: Mar. 22, 2011

(54) PANEL-TYPE SENSOR/SOURCE ARRAY ASSEMBLY

(75) Inventors: Matthew A. Herron, Palo Alto, CA (US); Bryan White, Fremont, CA (US); Jon H. LeFors, Burlingame, CA (US); Sam Truslow, San Francisco, CA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 1457 days.

(21) Appl. No.: 10/334,700

(22) Filed: Dec. 30, 2002

(65) Prior Publication Data
US 2004/0125916 A1 Jul. 1, 2004

(51) Int. Cl.
*A61B 5/05* (2006.01)
(52) U.S. Cl. ........ 600/409; 600/407; 600/425; 600/426; 600/427; 600/431; 600/436; 128/922; 700/245; 378/64; 378/65; 378/68; 378/204; 378/205; 324/207.11
(58) Field of Classification Search .............. 378/64–65, 378/68–69, 205, 207–208, 204; 600/422, 600/407, 409, 426–427, 425, 431, 436; 128/922; 700/245; 324/207.11
See application file for complete search history.

(56) References Cited

U.S. PATENT DOCUMENTS

| | | | | |
|---|---|---|---|---|
| 3,349,242 A | * | 10/1967 | Braestrup | 378/65 |
| 3,577,160 A | * | 5/1971 | White | 378/162 |
| 3,967,161 A | | 6/1976 | Lichtblau | |
| 3,969,629 A | * | 7/1976 | McIntyre | 378/65 |
| 4,023,167 A | | 5/1977 | Wahlstrom | |
| 4,114,601 A | | 9/1978 | Abels | |
| 4,123,749 A | | 10/1978 | Hartmann et al. | |
| 4,127,110 A | | 11/1978 | Bullara | |
| 4,160,971 A | | 7/1979 | Jones et al. | |
| 4,222,374 A | | 9/1980 | Sampson et al. | |
| 4,260,990 A | | 4/1981 | Lichtblau | |
| 4,393,872 A | | 7/1983 | Reznik et al. | |
| 4,618,822 A | | 10/1986 | Hansen | |
| 4,633,250 A | | 12/1986 | Anderson | |
| 4,642,786 A | | 2/1987 | Hansen | |
| 4,643,196 A | | 2/1987 | Tanaka et al. | |

(Continued)

FOREIGN PATENT DOCUMENTS

DE 19914455 A1 10/2000

(Continued)

OTHER PUBLICATIONS

International Search Report dated Jan. 24, 2003, PCT Application No. PCT/US02/29390.

(Continued)

*Primary Examiner* — Brian Casler
*Assistant Examiner* — James Kish
(74) *Attorney, Agent, or Firm* — Perkins Coie LLP

(57) ABSTRACT

A low-density sensor panel assembly system is provided for use with remote marker assemblies that generates a marker signal and for use with a radiation therapy source that generates a radiation beam during radiation therapy. The system includes a sensor array having a layer of sensor coils arranged in a selected pattern and configured to receive the marker signal from the remote marker. A support panel is connected to the sensor array and retains each of the sensor coils in a substantially fixed and unmoving position relative to the other sensor coils. The sensor panel and sensor array define a low-density panel structure configured to dwell in the radiation beam during the radiation therapy.

33 Claims, 5 Drawing Sheets

U.S. PATENT DOCUMENTS

| | | | |
|---|---|---|---|
| 4,696,287 A | 9/1987 | Hortmann et al. | |
| 4,745,401 A | 5/1988 | Montean | |
| 4,787,098 A * | 11/1988 | Silver | 378/18 |
| 4,795,995 A | 1/1989 | Eccleston | |
| 4,799,495 A | 1/1989 | Hawkins | |
| 4,909,789 A | 3/1990 | Taguchi et al. | |
| 4,936,823 A | 6/1990 | Colvin et al. | |
| 4,994,079 A | 2/1991 | Genese | |
| 5,019,713 A * | 5/1991 | Schmidt | 250/492.3 |
| 5,031,634 A | 7/1991 | Simon | |
| 5,057,095 A | 10/1991 | Fabian | |
| 5,062,847 A | 11/1991 | Barnes | |
| 5,095,224 A | 3/1992 | Renger | |
| 5,099,845 A | 3/1992 | Besz et al. | |
| 5,107,862 A | 4/1992 | Fabian et al. | |
| 5,142,292 A | 8/1992 | Chang | |
| 5,170,055 A | 12/1992 | Carroll et al. | |
| 5,189,690 A * | 2/1993 | Samuel | 378/162 |
| 5,216,255 A * | 6/1993 | Weidlich | 250/492.3 |
| 5,233,990 A * | 8/1993 | Barnea | 600/427 |
| 5,285,772 A * | 2/1994 | Rattner | 601/4 |
| 5,325,873 A | 7/1994 | Hirschi et al. | |
| 5,353,804 A | 10/1994 | Kornberg et al. | |
| 5,377,678 A | 1/1995 | Dumoulin et al. | |
| 5,386,191 A * | 1/1995 | McCarten et al. | 324/318 |
| 5,396,889 A * | 3/1995 | Ueda et al. | 600/407 |
| 5,396,905 A * | 3/1995 | Newman et al. | 600/422 |
| 5,400,787 A * | 3/1995 | Marandos | 600/422 |
| 5,409,004 A | 4/1995 | Sloan | |
| 5,423,334 A | 6/1995 | Jordan | |
| 5,425,367 A | 6/1995 | Shapiro | |
| 5,425,382 A | 6/1995 | Golden et al. | |
| 5,456,718 A | 10/1995 | Szymaitis | |
| 5,509,900 A | 4/1996 | Kirkman | |
| 5,528,651 A | 6/1996 | Leksell | |
| 5,559,435 A * | 9/1996 | Harada | 324/318 |
| 5,621,779 A * | 4/1997 | Hughes et al. | 378/65 |
| 5,638,819 A | 6/1997 | Manwaring et al. | |
| 5,664,582 A | 9/1997 | Szymaitis | |
| 5,680,106 A | 10/1997 | Schrott | |
| 5,697,384 A | 12/1997 | Miyawaki et al. | |
| 5,707,362 A | 1/1998 | Yoon | |
| 5,707,390 A | 1/1998 | Bonutti | |
| 5,727,552 A | 3/1998 | Ryan | |
| 5,731,996 A | 3/1998 | Gilbert | |
| 5,735,795 A | 4/1998 | Young et al. | |
| 5,745,545 A * | 4/1998 | Hughes | 378/65 |
| 5,764,052 A | 6/1998 | Renger | |
| 5,769,861 A | 6/1998 | Vilsmeier | |
| 5,810,851 A | 9/1998 | Yoon | |
| 5,815,076 A | 9/1998 | Herring | |
| 5,840,148 A | 11/1998 | Campbell | |
| 5,868,673 A | 2/1999 | Vesely | |
| 5,879,297 A | 3/1999 | Haynor et al. | |
| 5,910,144 A | 6/1999 | Hayashi | |
| 5,928,137 A | 7/1999 | Green et al. | |
| 5,951,481 A | 9/1999 | Evans | |
| 5,989,265 A | 11/1999 | Bouquet De La Joliniere et al. | |
| 6,026,818 A | 2/2000 | Blair | |
| 6,059,734 A | 5/2000 | Yoon | |
| 6,061,644 A | 5/2000 | Leis | |
| 6,067,465 A | 5/2000 | Foo et al. | |
| 6,076,008 A | 6/2000 | Bucholz | |
| 6,081,238 A | 6/2000 | Alicot | |
| 6,082,366 A | 7/2000 | Andra et al. | |
| 6,108,400 A * | 8/2000 | Siochi | 378/65 |
| 6,129,668 A * | 10/2000 | Haynor et al. | 600/424 |
| 6,165,135 A | 12/2000 | Neff | |
| 6,198,963 B1 | 3/2001 | Haim et al. | |
| 6,230,038 B1 * | 5/2001 | von Gutfeld et al. | 600/409 |
| 6,246,900 B1 | 6/2001 | Cosman et al. | |
| 6,307,473 B1 | 10/2001 | Zampini et al. | |
| 6,363,940 B1 | 4/2002 | Krag | |
| 6,371,379 B1 | 4/2002 | Dames | |
| 6,380,732 B1 | 4/2002 | Gilboa et al. | |
| 6,405,072 B1 * | 6/2002 | Cosman | 600/426 |
| 6,416,520 B1 | 7/2002 | Kynast et al. | |
| 6,474,341 B1 | 11/2002 | Hunter et al. | |
| 6,534,982 B1 | 3/2003 | Jakab | |
| 6,564,807 B1 | 5/2003 | Schulman et al. | |
| 6,611,141 B1 | 8/2003 | Schulz | |
| 6,675,810 B2 | 1/2004 | Krag | |
| 6,698,433 B2 | 3/2004 | Krag | |
| 6,701,179 B1 * | 3/2004 | Martinelli et al. | 600/424 |
| 6,812,842 B2 | 11/2004 | Dimmer | |
| 6,813,337 B2 * | 11/2004 | Svatos et al. | 378/65 |
| 6,822,570 B2 | 11/2004 | Dimmer et al. | |
| 6,838,990 B2 | 1/2005 | Dimmer | |
| 6,905,245 B2 * | 6/2005 | Cresens | 378/207 |
| 6,918,919 B2 | 7/2005 | Krag | |
| 6,965,792 B2 * | 11/2005 | Avrin et al. | 600/407 |
| 6,977,504 B2 | 12/2005 | Wright et al. | |
| 7,026,927 B2 | 4/2006 | Wright et al. | |
| 7,135,978 B2 | 11/2006 | Gisselberg et al. | |
| 2002/0091314 A1 | 7/2002 | Schlossbauer et al. | |
| 2002/0193685 A1 * | 12/2002 | Mate et al. | 600/424 |
| 2003/0066537 A1 | 4/2003 | Fabian et al. | |
| 2003/0088178 A1 | 5/2003 | Owens et al. | |
| 2003/0105394 A1 | 6/2003 | Fabian et al. | |
| 2003/0149353 A1 | 8/2003 | Boos | |
| 2003/0192557 A1 | 10/2003 | Krag et al. | |
| 2004/0133101 A1 | 7/2004 | Mate et al. | |
| 2004/0138555 A1 | 7/2004 | Krag | |
| 2004/0158146 A1 | 8/2004 | Mate et al. | |
| 2005/0059884 A1 | 3/2005 | Krag | |
| 2005/0195084 A1 | 9/2005 | Dimmer | |
| 2005/0261570 A1 | 11/2005 | Mate et al. | |

FOREIGN PATENT DOCUMENTS

| | | |
|---|---|---|
| EP | 0531081 A | 3/1993 |
| FR | 2635259 | 2/1990 |
| FR | 2686499 | 7/1993 |
| JP | 8166446 | 6/1996 |
| WO | WO 95/25475 | 9/1995 |
| WO | WO 97/12553 A | 4/1997 |
| WO | WO 98/30166 | 7/1998 |
| WO | WO 98/38908 A | 9/1998 |
| WO | WO 98/40026 | 9/1998 |
| WO | WO 99/30182 | 6/1999 |
| WO | WO 99/33406 | 7/1999 |
| WO | WO 99/40869 | 8/1999 |
| WO | WO 99/58044 | 11/1999 |
| WO | WO 99/58065 | 11/1999 |
| WO | WO 00/38579 | 7/2000 |
| WO | WO 00/51514 | 9/2000 |
| WO | WO 00/53115 | 9/2000 |
| WO | WO 00/65989 | 11/2000 |
| WO | WO 01/34049 | 5/2001 |
| WO | WO 02/39917 | 5/2002 |
| WO | WO 02/39918 | 5/2002 |
| WO | WO 02/100485 | 12/2002 |
| WO | WO-02100485 | 12/2002 |
| WO | WO 2004/060177 A1 | 7/2004 |
| WO | WO 2004/060475 A2 | 7/2004 |

OTHER PUBLICATIONS

U.S. Appl. No. 09/877,498, filed Jun. 8, 2001, Mate et al.
U.S. Appl. No. 10/382,123, filed Mar. 4, 2003, Newell et al.
U.S. Appl. No. 10/416,827, filed Nov. 17, 2000, Krag.
European Search Report for Application No. 03814943; Applicant: Calypso Medical Technologies, Inc.; Date of Mailing: Apr. 4, 2008 (2 pages).
International Search Report for Application No. PCT/US03/41140; Applicant Calypso Medical Technologies, Inc.; Date of Mailing: Jun. 1, 2007 (3 pages).
Kirsch S. et al. "Real Time Tracking of Tumor Positions for Precision Irradiation" Cars, Computer Assisted Radiology and Surgery. Proceedings of the International Congress and Exhibition. Proceedings of the International Symposium on Computer Assisted Radiology and Surgery, xx, xx, Jun. 24, 1998, pp. 262-264, XP001061283.

* cited by examiner

PANEL-TYPE SENSOR/SOURCE ARRAY ASSEMBLY

TECHNICAL FIELD

This invention relates to apparatus and methods used in association with radiation therapy, and more particularly, to systems for tracking markers and targets in three-dimensional space during radiation therapy.

BACKGROUND OF THE INVENTION

Systems have been developed to activate and detect remote activatable markers positioned, for example, in a selected item or object. The markers generate a signal used to detect the presence of the marker. Many of the activatable markers are hard-wired to a power source or other equipment external from the object. Other systems have been developed that utilize resonating leadless markers, also referred to as wireless active markers, positionable at or near a selected target. These wireless active markers are typically activated by a remote excitation source that generates a strong continuous excitation signal. The activated markers generate a detectable marker signal that must be distinguished from the strong continuous excitation signal and then analyzed to try to accurately determine the target's location. The process of distinguishing a weak marker signal from the strong continuous excitation signal, while maintaining sufficient accuracy and repeatability for determining the marker's location, has proven to be very difficult.

In the case of a verification device for medical tube placement, U.S. Pat. No. 5,325,873 to Hirschi et al. teaches a system that detects the general position of an object within a body of tissue. The detection system includes a three-axis resonant-circuit target attached to the object. A separate remote hand-held detection probe has a pair of parallel and coaxially aligned transmitter/sensing coils. The transmitter sensing coils generate a current that determines whether a return signal strength of the target is great enough to be counted as a valid signal. The hand-held detection probe also has a pair of receiver coils positioned within each of the transmitter coils and connected in a series-opposed fashion. The hand-held detection probe also has a visual display coupled to the receiver coils and configured to indicate the direction in which the probe should be moved to center the detection probe over the selected object. While the system of Hirschi et al. is usable to detect the presence of an object in a body, the system is not usable for tracking and monitoring an object in real time during radiation therapy treatment.

Recent advances in radiation therapy are providing new avenues of effective treatment for localized cancer after the cancer's position has been determined. The treatments include 3D conformal external beam radiation, inverse modulated radiation therapy (IMRT), stereotactic radiosurgery and brachytherapy. These newer treatment modalities deliver greater doses of radiation to a tumor, which accounts for their increased effectiveness when compared to traditional standard external beam irradiation.

A dose response relationship for radiotherapy exists for most cancers, so dose escalation is often necessary to achieve continued improvements in the management of localized cancers with radiotherapy. As the radiation dose is increased, the volume of adjacent normal tissue irradiated around the cancerous target can be decreased by maintaining a tighter treatment margin around the target. The size of the treatment margin, however, must be sufficient to accommodate potential tumor motion before or during radiation therapy. As an example, movement of a tumor in the prostate often occurs during radiation treatment primarily due to patient breathing, rectal and bladder filling and emptying, which consequently move the prostate. Accordingly, it is highly desirable to monitor actual tumor motion in real time during the delivery of radiation therapy to minimize treatment margins while ensuring that the tumor does not move out of the treatment volume.

It is known that the introduction of solid materials in the path of a high energy photon or radiation beam during radiation therapy displaces electrons from the solid materials. To a lesser extent, such interaction also generates secondary photons of lower energy than the primary photons of the radiation beam. The displaced electrons and secondary photos are scatter products that contaminate the beam. Because the scatter products have a lower energy than the primary photons, the scatter products more readily damage superficial tissues of the body, such as the dermis and the subcutaneous layer, than do the primary photons. The primary photons in the beam penetrate the patient to irradiate the target, but damage to the superficial tissues by scatter products may limit the total dose that can be delivered to the patient.

It is also known that the high energy radiation therapy photon beam is attenuated as it passes through solid materials in its path. Managing radiation treatments includes defining the geometry of a plurality of radiation fields to be used in the treatments and specifying the radiation dose to be delivered with each of the fields. This stage of treatment management is referred to as "treatment planning," and the control and measurement of dose distribution is termed "dosimetry." Attenuation of the therapy beam by solid materials, such as beam filters and other accessories, is typically included in the computations of dose distribution in the target tissue in the treatment planning process.

A further implication of the attenuation caused by components dwelling in the radiation beam is the appearance of artifacts in x-ray images collected for the purpose of verifying patient positioning. For example, structural details of the components in the path of the radiation used for imaging will appear in the images.

In light of the problems of beam contamination and attenuation, it is not desirable to place structures in the path of the radiation beam unless the benefits of doing so outweigh the resulting contamination and attenuation. For example, it is often necessary to position patient tabletops, blocking beam trays, and immobilization devices in the radiation beam during radiation therapy. Accordingly, even though it may be desirable to position additional equipment in the radiation beam, this is difficult because of the additional beam contamination and/or attenuation.

SUMMARY OF THE INVENTION

Under one aspect of the invention, a system and method is provided for accurately locating and tracking the position of a target within a body in real time during radiation therapy while controlling beam contamination and/or attenuation. In one embodiment a signal measurement system is provided for use with a remote marker that generates a marker signal and a radiation therapy source that generates a radiation beam. The system comprises an array of sensor coils configured to receive the marker signal from the remote marker and a support panel connected to the array of sensor coils. The support panel and the array of sensor coils define a sensor assembly that dwells in the radiation beam and is at least substantially rigid. The sensor assembly is configured to limit an increase in a skin dose of the radiation beam through the panel assembly up to approximately 80% more than a skin dose of the radiation beam through air, and in many embodiments the increase in skin dose is limited to 50%. In one embodiment the sensor panel assembly has a mass per unit area in a plane of the support panel of approximately 1.0 grams/cm² or less.

Under another aspect of the invention, a method is provided for locating a target in a patient and irradiating the target with a radiation beam. In one embodiment the method comprises positioning a marker at a selected location relative to the target. A sensor panel assembly is positioned adjacent to the patient. The marker is energized to generate a marker signal, and the marker signal is received by the sensor panel assembly. The location of the marker and the target are determined in real time in three-dimensional space based upon the marker signal received by the sensor panel assembly. Radiation therapy is delivered to the target with the radiation beam passing through the sensor panel assembly before irradiating the target.

DETAILED DESCRIPTION OF THE INVENTION

In the following description, certain specific details are set forth in order to provide a thorough understanding of various embodiments of the invention. However, one skilled in the art will understand that the invention may be practiced without some of these details. In other instances, well-known structures associated with magnetic excitation systems, sensor systems, resonating markers, activators, linear accelerators, and patient supports have not been shown or described in detail to avoid unnecessarily obscuring the description of the embodiments of the invention. FIGS. 1-10 illustrate a system and components of a signal measurement system with a source/sensor panel assembly in accordance with embodiments of the present invention. Several of the components described below with references to FIGS. 1-10 can also be used in systems for performing methods in accordance with aspects of the present invention. Therefore, like reference numbers refer to like components and features throughout the various figures.

Figure 1:
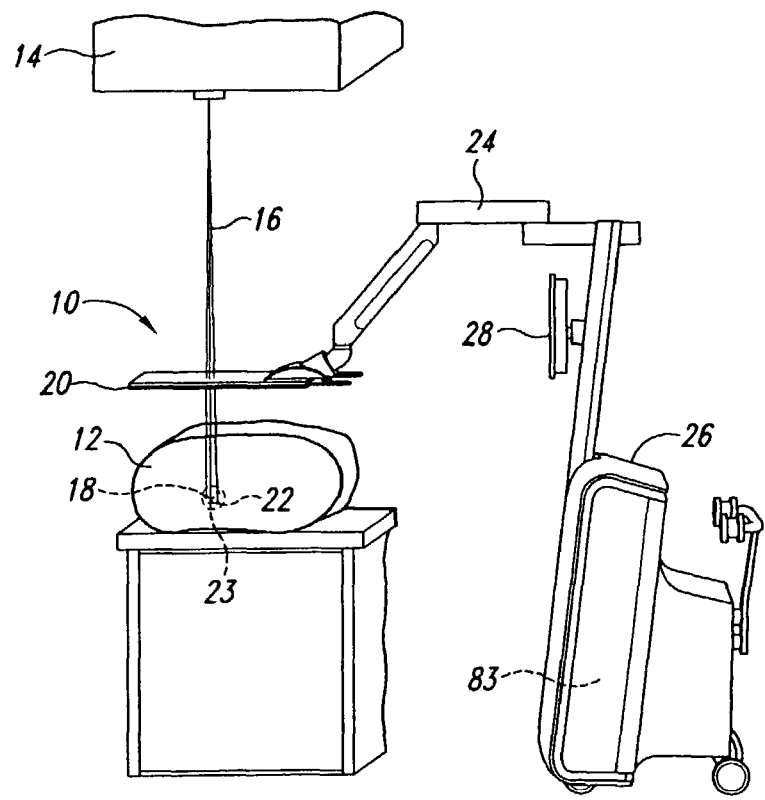
FIG. 1 is an isometric view of a signal measurement system with a source/sensor panel assembly in accordance with one embodiment of the invention, the panel assembly being shown positioned between a patient and a linear accelerator.

FIG. 1 is a schematic isometric view of a signal measurement system 10 in accordance with one embodiment of the present invention. The signal measurement system 10 is illustrated with a generally flat source/sensor panel assembly 20 positioned between a patient 12 (shown schematically) and a linear accelerator 14. The linear accelerator 14 is configured to deliver a radiation beam 16 to a selected target 18 in the patient 12. The panel assembly 20 is configured to dwell in the radiation beam 16 during delivery of radiation therapy to the target 18 while minimizing beam attenuation and/or contamination during the radiation therapy.

The panel assembly 20 is configured to track a plurality of leadless markers 22 positioned in or on the patient 12 at selected positions relative to the target 18. Several embodiments of markers 22 are described in detail in co-pending U.S. patent application Ser. No. 09/954,700, entitled "Miniature Resonating Marker Assembly," filed Sep. 14, 2001, which is incorporated herein in its entirety by reference thereto. The markers 22 are energized by a magnetic excitation field generated by a plurality of source coils in the panel assembly 20, which are discussed in greater detail below. Additional details about generating the excitation field with a plurality of source coils are discussed in co-pending U.S. patent application Ser. No. 10/213,908, entitled "System for Excitation of a Leadless Miniature Marker," filed Aug. 7, 2002, which is also incorporated herein in its entirety by reference thereto.

Each of the energized markers 22 generates a marker signal that is detected by the panel assembly 20. Based upon data from the marker signals, the signal measurement system 10 calculates the actual, real time location of the markers 22 and the target 18 in three-dimensional space relative to a fixed reference frame. The actual, real time location of the target 18 can then be monitored and compared to the known position of a beam isocenter 23 of the radiation beam before and during delivery of the radiation therapy to the target in the patient 12. The position of the target 18 can be monitored and adjusted as needed so the target's isocenter is substantially coincident with the beam isocenter 23 for precise and accurate irradiation of the target 18. The accurate real time monitoring of the location of the target isocenter allows smaller treatment margins to be used.

The panel assembly 20 of the illustrated embodiment is operatively connected to an articulating arm 24 of a moveable module 26 of the signal measurement system 10. A monitor 28 is connected to the movable module 26 and is configured to provide selected data to an operator. As an example, the monitor 28 could display information about the position of the panel assembly 20, the target 18, and the markers 22 relative to the radiation beam's isocenter 23 during patient setup for the radiation therapy.

Figure 2:
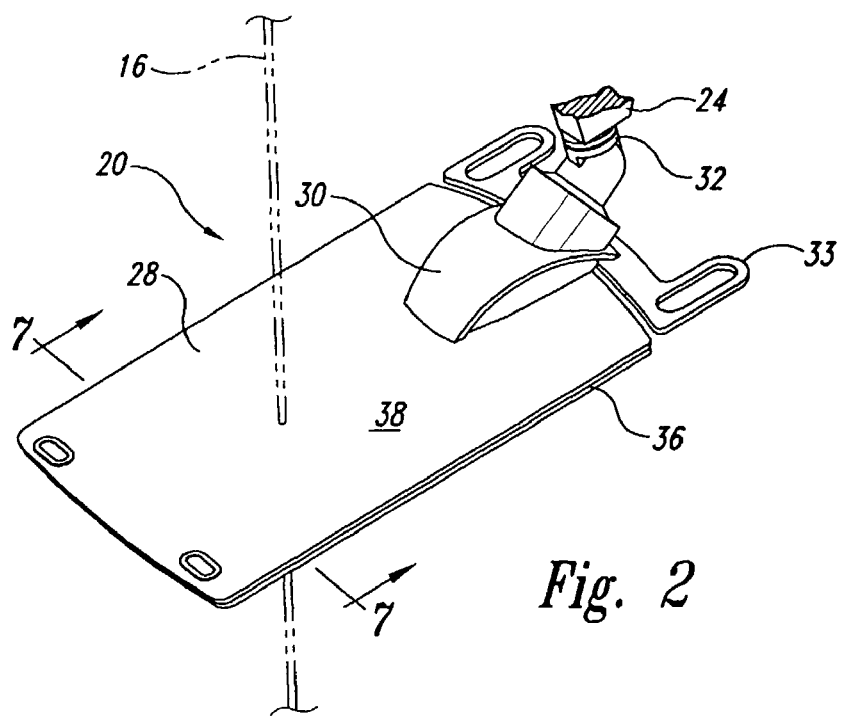
FIG. 2 is an enlarged isometric view of the panel assembly of FIG. 1.

FIG. 2 is an enlarged top isometric view of the panel assembly 20 of FIG. 1. The panel assembly 20 of the illustrated embodiment has a substantially planar panel portion 28 connected to a mounting structure 30. The mounting structure 30 is connected to an adjustable distal end 32 of the articulating arm 24. The panel assembly 20 has a pair of positioning handles 33 connected to the mounting structure 30 and configured to allow for easy positioning of the panel assembly 20 (e.g., relative to the patient 12 (FIG. 1)). The panel portion 28 is a substantially rigid, low-density laminated structure that contains source and sensor coils for excitation of the leadless markers 22 (FIG. 1) and for monitoring the marker's position in three-dimensional space during radiation therapy, as discussed in greater detail below. The rigid, low-density panel portion 28 is configured to reside in the radiation beam 16 during radiation therapy with an acceptable amount of beam attenuation and/or entrainment of secondary electrons.

Figure 3:
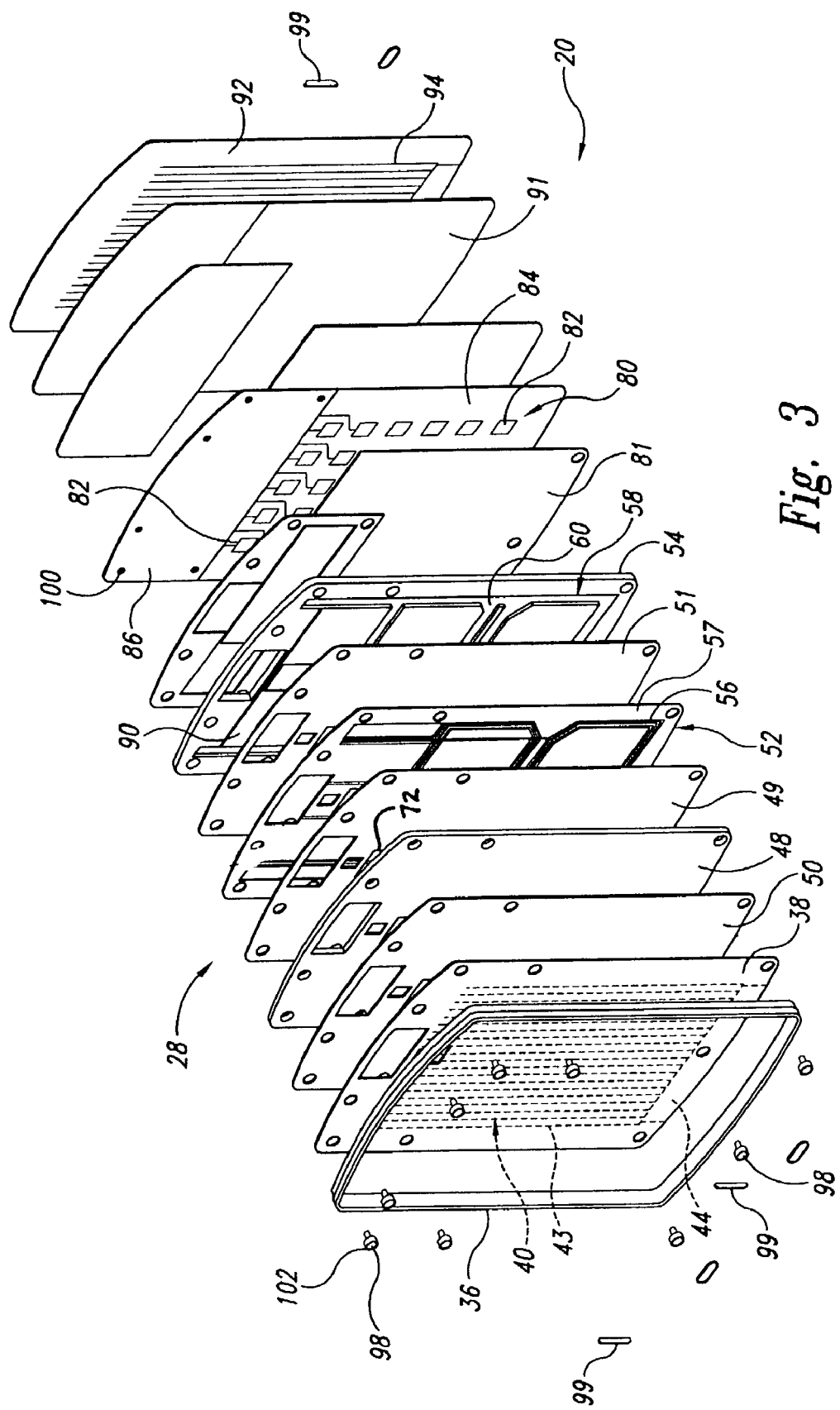
FIG. 3 is a reduced exploded isometric view of the panel assembly of FIG. 2.

FIG. 3 is an exploded isometric view of the panel portion 28 of the panel assembly 20 of FIG. 1. The panel portion 28 is constructed with a plurality of layers laminated together and surrounded by a flexible perimeter strip 36. The panel portion 28 has a thin first outer skin 38 that forms an outer surface of the panel portion. The first outer skin 38 is a durable material that is thermally stable over the operating temperatures that can occur within the panel assembly 20. The first outer skin 38, in one embodiment, is a thin Kevlar or Thermount film that can accept printing of logos, text, pictures, instructions, etc. so as to be visible from the exterior of the panel portion 28.

In one embodiment the first outer skin 38 has electric shielding 40 printed or otherwise attached to its inner surface. The electric shielding 40 blocks undesirable external electric fields from reaching the sensor coils. The electric shielding 40 is adapted to prevent or minimize the presence of eddy currents during the operation of the panel assembly 20 caused by the internal source coils 56 or external electric fields. This can be important in some embodiments because eddy currents could interfere with the panel assembly 20 accurately determining the location of the markers 22 (FIG. 1) with a high degree of repeatability. The electric shielding 40 of the illustrated embodiment includes a ground portion 44 and a plurality of parallel legs 43 of gold-plated, copper strips extending from the ground portion to define a comb-shaped shielding. Although the top skin 38 in the illustrated embodiment is formed by a thin Kevlar or Thermount layer, and the electric shielding 40 is formed by the gold-plated, copper material, alternate embodiments may use other suitable materials for these components.

The top skin 38 is adhered to a flat surface of a first low-density stiffening spacer panel 48. The top skin 38, in one embodiment, is adhered to the spacer panel 48 with a layer 50 of pressure sensitive adhesive, although other adhesives such as temperature sensitive adhesives can be used in other embodiments. The spacer panel 48 of the illustrated embodiment is a stiff, low-density foam material, such as a 3.25 lb. density, closed-cell Rohacell foam, having a thickness of approximately 1.036 cm (0.408 in.). Alternate embodiments can use other low-density, thermally stable material with a selected thickness. This low-density foam spacer panel 48, when provided in the laminated structure, forms a very stiff, thermally stable layer capable of withstanding the temperatures generated within the panel portion 28 with substantially no thermal expansion, contraction, or other shape change during operation of the panel assembly 20.

The first spacer panel 48 is also laminated with an adhesive layer 49 to one side of a substantially planar array 52 of source coils 56. The other side of the source coil array 52 is laminated with an adhesive layer 51 to a second low-density stiffening spacer panel 54. Accordingly, the source coil array 52 is laminated between the first and second spacer panels 48 and 54. In the illustrated embodiment, the second spacer panel 54 is also made of the low-density, Rohacell foam and has a thickness of approximately 1.255 cm (0.494 in). Alternate embodiments, however, can use other low-density, thermally stable materials of a selected thickness for the second spacer panel 54.

Figure 4:
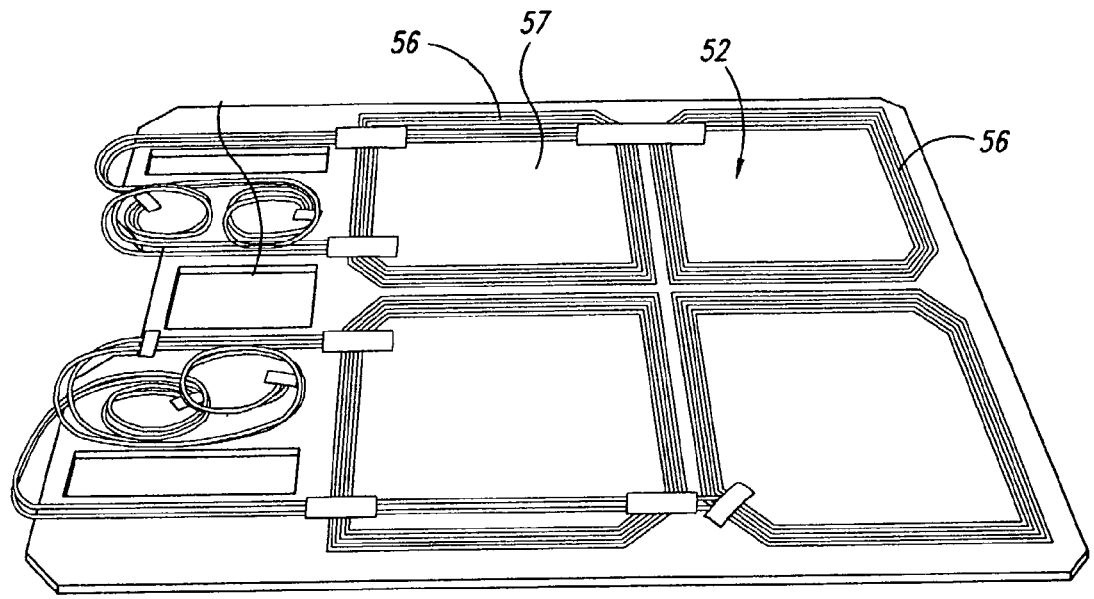
FIG. 4 is an enlarged top isometric view of an array of source coils shown removed from the panel assembly of FIG. 2.

FIG. 4 is an enlarged top isometric view of the source coil array 52 shown removed from the panel assembly 20 of FIG. 3. The source coil array 52 includes a plurality of substantially planar source coils 56, also referred to as excitation coils.

Each source coil 56 is formed by a winding of a selected insulated wire, such as a Litz wire. The source coils 56 are adapted to carry high currents so that each source coil can generate a magnetic field within a selected volume around the panel assembly 20 (FIG. 2) to energize the leadless markers 22 (FIG. 1) located with that volume. Co-pending U.S. patent application Ser. No. 10/213,980, entitled "System for Excitation of a Leadless Miniature Marker Assembly," filed Aug. 7, 2002, provides additional information about systems to create shaped magnetic excitation fields adapted to excite and energize the remote leadless markers 22.

The source coil array 52 of the illustrated embodiment has four substantially planar source coils 56 adjacent to each other and electrically isolated from each other. The source coils 56 are partially embedded in one side of a thin, thermally stable, low-density substrate 57. In one embodiment the substrate 57 is a closed-cell foam material, such as the Rohacell foam or other suitable material. As best seen in FIG. 3, when the source coil array 52 is laminated between the first and second spacer panels 48 and 54, the source coils 56 face the first spacer panel 48 and the back side of the substrate 57 faces the second spacer panel 54. When electrical current is directed through the source coils 56, each source coil can generate a significant amount of heat.

Figure 6:
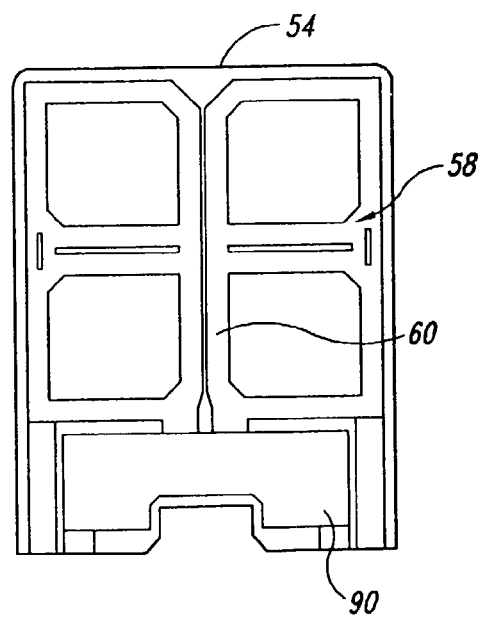
FIG. 6 is a plan view of a second stiffening spacer shown removed from the panel assembly of FIG. 2 and showing another portion of the coil-cooling system.
Figure 7:
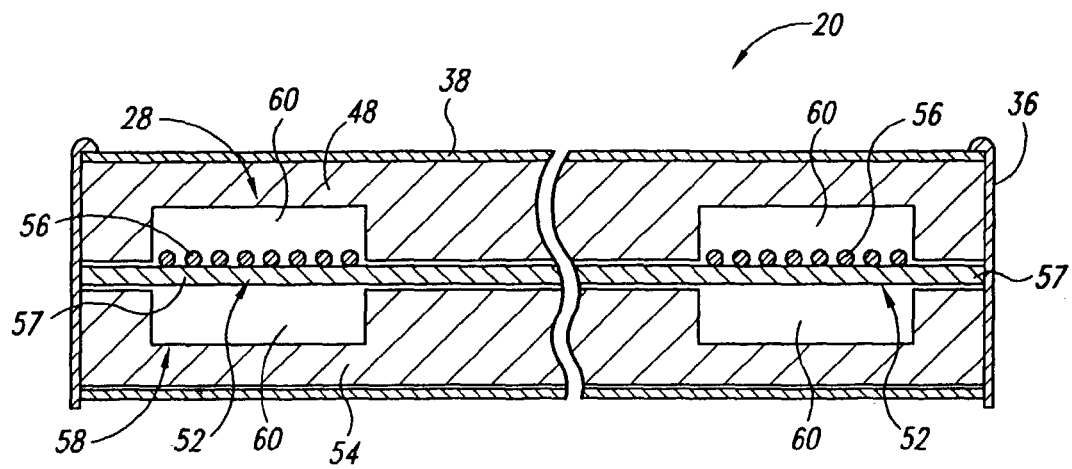
FIG. 7 is an enlarged cross-sectional view taken substantially along line 7-7 of FIG. 2.
Figure 8:
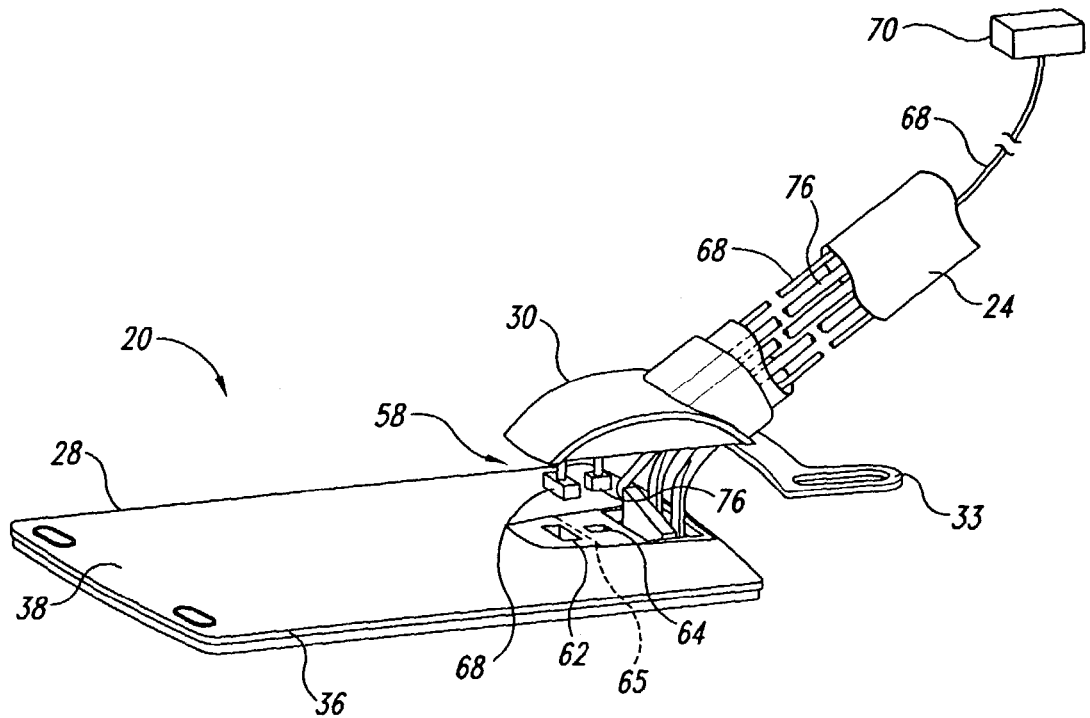
FIG. 8 is a partially exploded isometric view of the panel assembly of FIG. 2 showing air and power lines connected to the panel assembly.

The first spacer panel 48 (FIG. 5) includes an airflow inlet 66 that receives a flow of cooling air from an air inlet port 62 (FIG. 8). The air flows from the air inlet port 62 into the cooling channels 60 in the first spacer panel 48, and the cooling channels carry the air along a path adjacent to the source coils 56 (FIG. 7). The air also flows from the air inlet port 62, through an aperture 72 in the substrate 57 of the source coil array 52 (FIGS. 3 and 4) and into the cooling channels 60 in the second spacer panel 54 (FIGS. 6 and 7). Accordingly, the flow of air from the air inlet port 62 is directed into the cooling channels 60 on both sides of the source coil array 52 and along a path corresponding to the shapes of the source coils 56. The flow of air over the source coils 56 carries heat away from the source coils during operation of the panel assembly 20. The flow of heated air exits the cooling channels 60 through an airflow outlet 67 that communicates with the air outlet port 64 (FIG. 8) and the exhaust air hose 76. Accordingly, the temperature change within the panel portion 28 can be maintained within the range of approximately 10° C. According to alternative embodiments of the invention, a cooling fluid may be used in the coil-cooling system to cool the panel portion 28. In accordance with this embodiment, a coolant pump may be coupled to the support panel in lieu of the air pump 70 to circulate the cooling fluid in the coil-cooling system.

The air flows through the panel portion 28 as discussed in greater detail below, and exits from the interior of the panel portion through an air outlet port 64. In one embodiment an air flow shield 65 is provided between the air inlet port 62 and the air outlet port 64 to block the airflow from prematurely flowing directly into the air outlet port before flowing through the panel portion 28 to cool the source coils 56. The air outlet port 64 exhausts air through the mounting portion 30 and into or along the articulating arm 24. In the illustrated embodiment, the exhaust air vents to ambient air through the articulating arm, although the exhaust air can be directed all the way back to the movable module 26 in alternate embodiments.

Figure 5:
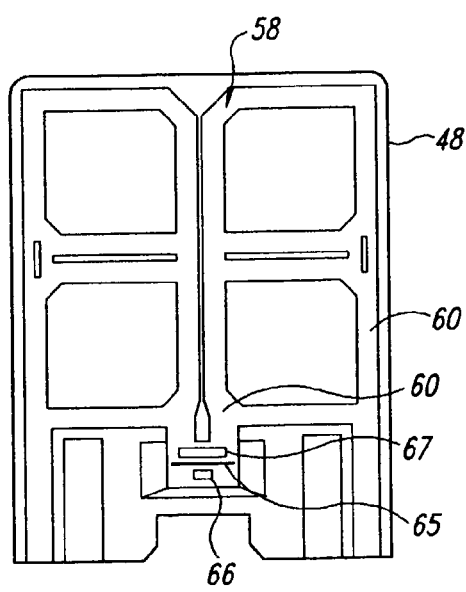
FIG. 5 is a plan view of a first stiffening spacer shown removed from the panel assembly of FIG. 2 and showing a portion of an integral coil-cooling system.

FIG. 5 is a plan view of one side of the first spacer panel 48 that faces the source coil array 52 of FIG. 4 and includes a portion of the coil-cooling system 58. FIG. 6 is a plan view of the side of the second spacer panel 54 that also faces the source coil array 52 of FIG. 4, and that includes another portion of the coil-cooling system 58. FIG. 7 is an enlarged partial cross-sectional view taken substantially along line 7-7 of FIG. 2 showing the first and second spacer panels 48 and 54 with the source coil array 52 between the spacer panels and adjacent to the coil-cooling system 58. The coil-cooling system 58 of the illustrated embodiment has by a plurality of cooling channels 60 integrally formed in the foam spacer panels 48 and 54. The cooling channels 60 define airflow passageways defining a shape generally corresponding to the location of the source coils 56 between the first and second spacer panels 48 and 54.

The first spacer panel 48 (FIG. 5) includes an airflow inlet 66 that receives a flow of cooling air from an air inlet port 62 (FIG. 8). The air flows from the air inlet port 62 into the cooling channels 60 in the first spacer panel 48, and the cooling channels carry the air along a path adjacent to the source coils 56 (FIG. 7). The air also flows from the air inlet port 62, through an aperture 72 in the substrate 57 of the source coil array 52 (FIGS. 3 and 4) and into the cooling channels 60 in the second spacer panel 54 (FIGS. 6 and 7). Accordingly, the flow of air from the air inlet port 62 is directed into the cooling channels 60 on both sides of the source coil array 52 and along a path corresponding to the shapes of the source coils 56. The flow of air over the source coils 56 carries heat away from the source coils during operation of the panel assembly 20. The flow of heated air exits the cooling channels 60 through an airflow outlet 67 (FIG. 5) that communicates with the air outlet port 64 (FIG. 8) and the exhaust air hose 76. Accordingly, the temperature change on the surface of the panel portion 28 can be maintained within the range of approximately 10° C. of ambient.

Referring again to the exploded view of FIG. 3, the laminated assembly 20 includes a sensor coil array 80 adhered to a flat side of the second spacer panel 54 opposite the airflow channels 60. Accordingly, the second spacer panel 54 is laminated between the sensor coil array 80 and the source coil array 52. The sensor coil array 80 of the illustrated embodiment is adhered to the second spacer panel 54 with a layer 81 of pressure sensitive adhesive, although other adhesives may be used in alternate embodiments.

Figure 9:
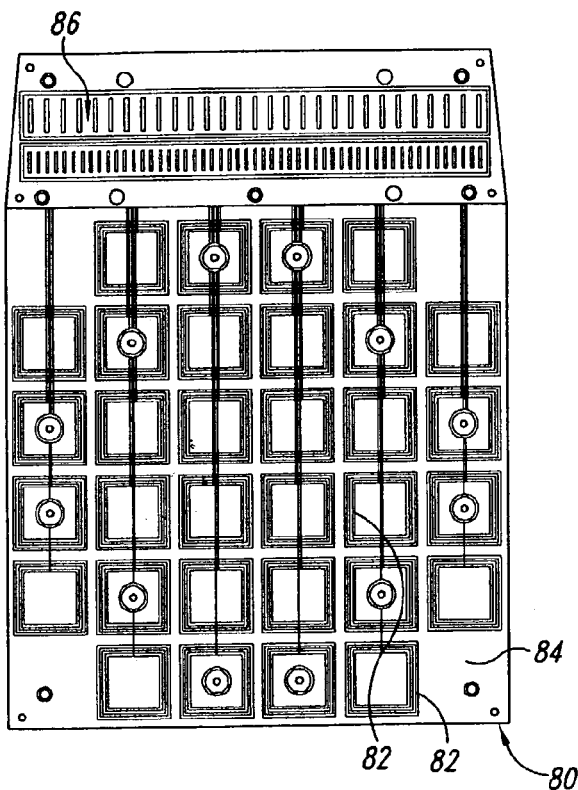
FIG. 9 is an enlarged plan view of an array of sensor coils shown removed from the panel assembly of FIG. 2.

FIG. 9 is an enlarged plan view of the sensor coil array 80 shown removed from the panel assembly 20 of FIG. 2. The sensor coil array 80 includes a plurality of substantially planar sensor coils 82 arranged in a selected pattern on a thin substrate 84. In one embodiment the sensor coils 82 are printed circuit windings on the substrate 84, which is formed by a thin layer of Kapton film having a thickness of approximately 0.030 inches. The Kapton film is a durable, highly dielectric material and is thermally stable over the operating temperatures within the panel assembly 20. Accordingly, the substrate 84 will not substantially expand or contract in response to temperature changes in the panel assembly 20, thereby substantially preventing creep in the position of the sensor coils 82 relative to each other and relative to the outer surfaces over time. Preventing creep of the sensor coils 82 can help maintain the high degree of repeatability and accuracy of the panel assembly 20. Although the illustrated embodiment uses a Kapton film for the substrate 84, other durable, thermally stable materials can be used in alternate embodiments.

The sensor coil array 80 of the illustrated embodiment includes thirty-two flat sensor coils 82 electrically isolated from each other. The sensor coils 82 are connected to a plurality of preamplifiers and other control circuitry 86 carried on one end of the substrate 84. While the illustrated embodiment includes thirty-two sensor coils 82, alternate embodiments can have a different number of the sensor coils 82 arranged in a selected pattern. In addition, the illustrated embodiment shows a substantially flat sensor coil array 80, although alternate embodiments can provide a rigid, planar sensor coil array having an arched or slightly curved shape.

The substrate 84 with the sensor coils 82 thereon are laminated onto the second spacer panel 54 (FIG. 3) such that the sensor coils are retained in a fixed position within the laminated panel assembly 20 so they do not move relative to each other, or the outer surfaces, during operation of the target tracking system 10. The sensor coils 82 are configured to receive a marker signal from one or more of the energized leadless markers 22 within a patient 12 (FIG. 1), and each sensor coil generates a sensor signal based upon data from the marker signal. The sensor signals are processed via a central processing unit 83 (FIG. 1) in the module 26 of the signal measurement system 10 to determine the precise location of the leadless marker 22 and the associated target 18 in three-dimensional space relative to a fixed and known reference frame.

During operation of the panel assembly 20, the control circuitry 86 on the sensor coil array 80 also generates some heat. In the illustrated embodiment, the control circuitry 86 is positioned adjacent to an enlarged aperture 90 formed in the second spacer panel 54. The enlarged aperture 90 is positioned so that the flow of cooling air in the coil-cooling system 58 is directed across the control circuitry 86 before the cooling air flows into the air outlet port 64 discussed above. Accordingly, the coil-cooling system 58 also draws heat away from the control circuitry 86 during operation of the panel assembly 20 to maintain an acceptable operating temperature within the panel assembly.

Referring again to FIG. 3, the sensor coil array 80 is laminated between the second spacer panel 54 and a thin, low-density foam spacer panel 91. The spacer panel 91 in the illustrated embodiment is a thin sheet of Rohacell foam, although other materials can be used. The spacer panel 91 is laminated to a thin second outer skin 92. The second outer skin 92 of the illustrated embodiment is a thin Kevlar or Thermount film having substantially the same construction as the first outer skin 38 discussed above. An electric shielding 94 substantially identical to the electric shielding 40 discussed above is provided on one side of the second outer skin 92. The second outer skin's electric shielding 94 works with the first outer skin's electric shielding 40 to minimize the creation of eddy currents in the panel assembly 20, and to block undesirable external electric fields from reaching the sensor coils.

The multiple layers of the panel assembly 20 described above form a very stiff, yet lightweight laminated structure that fixedly retains the source coils 56 in one layer and the sensor coils 82 in another layer. This stiff laminated panel assembly 20 is constructed so it does not substantially deflect across its surface during operation of the panel assembly. In the illustrated embodiment, the panel assembly 20 is configured to retain the sensor coil array 80 in the fixed position with a deflection of no greater than ±0.5 mm, and in some cases no more than ±0.3 mm. The stiffness of the lightweight laminated panel assembly 20 allows for very accurate and repeatable monitoring of the precise location of the leadless markers 22 (FIG. 1) in real time during the radiation therapy.

The materials used in the laminated panel assembly 20, particularly the low-density foam spacer panels 48 and 54, provide a panel portion 28 with a low mass per unit area in the plane of the sensor coil layer, also referred to as the "mass-density" of the panel assembly. In one embodiment the mass-density is measured by the amount of mass in a square centimeter column through the thickness of the panel assembly 20 orthogonal to the sensor coil layer. A lower mass of material in the column results in less contamination of the radiation beam 16. The panel assembly 20 is constructed to have a low mass-density to allow the panel assembly to dwell in the radiation beam 16 during delivery of radiation therapy to the patient 12 without excessive beam contamination. In the illustrated embodiment, the panel assembly 20 has a thickness of approximately 2.54 cm, and the mass-density of the panel portion 28 is in the range of approximately 1.0 gram/cm$^2$ or less. In one embodiment the panel portion 28 of the panel assembly 20 has a mass-density that averages approximately 0.3 grams/cm$^2$ or less over the entire area of the panel that normally resides directly in the path of the radiation beam.

The laminated panel assembly 20 of the illustrated embodiment is also configured to result in a beam attenuation of approximately only 0.5% or less while dwelling in the radiation beam during radiation therapy. Because the panel assembly 20 introduces a mass through which the radiation beam 16 will pass before reaching the patient 12, the panel assembly will still cause some secondary scatter products to be entrained in the radiation beam 16, which will increase the amount of radiation applied to the skin and surface tissue of the patient (referred to as a skin dose). The skin dose is higher when the radiation beam 16 passes through the panel assembly 20 before reaching the patient 12 compared to the skin dose when the radiation beam passes through only air. Yet, because the panel assembly 20 has a low mass-density, it can dwell in the radiation beam 16 during therapy to provide the real time information about the target location while only increasing the skin dose to the patient 12 up to approximately 80% more than the skin dose of the radiation beam through air alone. In other embodiments, the panel assembly 20 is configured to increase the skin dose up to approximately 40-60%, or on average about 50%.

The panel assembly 20 of the illustrated embodiment with a low mass-density configuration also provides the additional benefit of being able to dwell in an x-ray beam during an x-ray imaging procedure while providing only minimal artifacts to the x-ray film. Accordingly, the panel assembly 20 can be used to track and monitor a target's location in real time during x-ray imaging, such as may occur during patient setup for radiation therapy.

Figure 10:
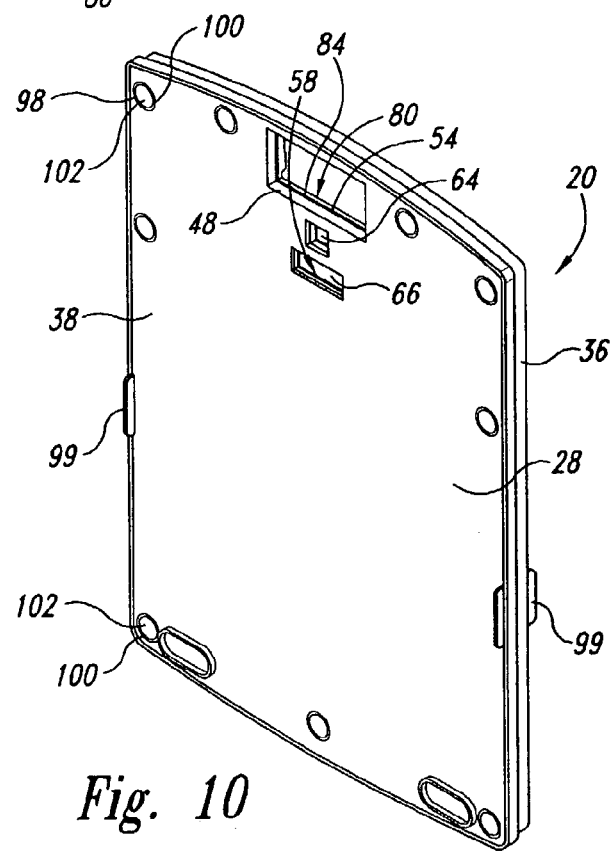
FIG. 10 is an enlarged isometric view of the panel assembly of FIG. 3 showing a plurality of optical targets and alignment flags.

FIG. 10 is an isometric view of the panel assembly 20 with the mounting portion not illustrated for purposes of clarity. The panel assembly 20 includes a plurality of optical targets 98 visible from a remote location exterior of the panel assembly. The optical targets 98 provide visual positioning mechanisms that allow the panel assembly 20 to be located within a treatment room or the like by an external optical tracking system.

In the illustrated embodiment, the optical targets 98 include LEDs 100 that generate infrared light (approximately 850 nanometers). The LEDs 100 are mounted on the substrate 84 of the sensor coil array 80 and receive power from the control circuitry 86 discussed above. The first spacer panel 48 has a plurality of apertures aligned with the LEDs 100. A plurality of diffusion elements 102 are bonded to the top skin 38 in alignment with the LEDs 100 to enhance the visibility of the light from the LEDs by the optical positioning system. In one embodiment the diffusion elements 102 are configured to provide substantially equal light dispersion even at an angle as low as 10 degrees to the surface for accurate registration and detection by the optical positioning system in a radiation therapy treatment room or the like. Accordingly, the position of the panel assembly 20 can be accurately established and monitored by the optical targets 98 relative to a selected external reference frame, such as in the radiation therapy treatment room, to ensure that the position of the panel assembly remains at a known location relative to the linear accelerator isocenter during the patient setup and radiation therapy.

Although specific embodiments of, and examples for, the present invention are described herein for illustrative purposes, various equivalent modifications can be made without departing from the spirit and the scope of the present invention, as will be recognized by those skilled in the relevant art. The teachings provided herein of the present invention can be applied to systems for excitation of leadless miniature markers, not necessarily the exemplary system generally described above. Accordingly, the invention is not limited except as by the appended claims.

We claim:

1. A signal measurement system for use with a remote marker that generates a marker signal, and a radiation therapy source that generates a radiation beam, comprising:
    an array of sensor coils arranged in a selected pattern and configured to receive the marker signal from the remote marker; and
    a movable support panel connected to the array of sensor coils, the support panel and the array of sensor coils defining a sensor assembly that is at least substantially rigid and has a mass per unit area in a plane of the support panel of approximately 1.0 grams/cm$^2$ or less, wherein the movable support panel is operably connected to an articulating arm of a moveable module of the signal measurement system.

2. The system of claim 1 wherein the sensor assembly has a mass per unit area in a plane of the support panel that averages approximately 0.3 grams/cm$^2$ or less for the entire volume.

3. The system of claim 1 wherein the array of sensor coils is embedded within the support panel.

4. The system of claim 1 wherein the array of sensor coils defines a first layer, and the signal measurement system further comprises a plurality of source coils forming a second layer connected to the support panel and spaced apart from the first layer.

5. The system of claim 4 wherein the support panel includes an integral coil-cooling system coupled to the plurality of source coils.

6. The system of claim 5 wherein the coil-cooling system includes a cooling channel integrally formed in the support panel adjacent to the plurality of source coils and configured to remove heat from the plurality of source coils.

7. The system of claim 1 wherein the array of sensor coils comprises a substrate, and the sensor coils are printed circuit windings on the substrate, and the substrate is laminated to the support panel.

8. The system of claim 1, further comprising a layer of source coils coupled to the support panel.

9. The system of claim 1 wherein the support panel includes a first foam core and a second foam core, and the signal management system further comprises a layer of source coils laminated between the first and second foam cores, the array of sensor coils being spaced apart from the layer of source coils by at least one of the first and second foam cores.

10. The system of claim 1, further comprising an optical target coupled to the support panel.

11. The system of claim 1 wherein the support panel includes an integral coil-cooling system coupled to the plurality of source coils.

12. A low-density signal measurement system for use with a remote marker that generates a marker signal and a radiation therapy source that generates a radiation beam, comprising:

an array of sensor coils arranged in a selected pattern and configured to receive the marker signal from the remote marker; and a moveable support panel laminated to the array of sensor coils to form a sensor assembly that retains the sensor coils in a fixed arrangement, wherein the sensor assembly is configured to attenuate the radiation beam by 0.5% or less, wherein the movable support panel is operably connected to an adjustable arm of a base assembly of the signal measurement system.

13. The system of claim 12 wherein the sensor assembly has a mass per unit area in a plane of the support panel that averages approximately 0.3 grams/cm$^2$ or less.

14. A signal measurement system for use with a linear accelerator that generates a radiation beam and marker that generates a marker signal, comprising:

a first coil layer having substantially planar source coils;

a second coil layer having substantially planar sensor coils configured to receive the marker signal from the marker upon excitation of the marker; and a free-standing support panel carrying the first and second coil layers with the source coils and sensor coils in a substantially rigid fixed position relative to each other, the support panel and the first and second coil layers defining a laminated sensor assembly configured to allow the radiation beam to pass therethrough with a radiation beam attenuation of approximately 0.5% or less, wherein the support panel is operably connected to an arm of a moveable base of the signal measurement system.

15. The system of claim 14 wherein the support panel has an integral coil-cooling system.

16. The system of claim 14, further comprising a first stiffening spacer and a second stiffening spacer, the first coil layer being laminated between the first and second stiffening spacers, and one of the first and second stiffening spacers being between the first and second coil layers.

17. The system of claim 14 wherein the first and second coil layers are substantially parallel.

18. The system of claim 14 wherein the first and second coil layers are embedded in the laminated sensor assembly.

19. A system for locating a remote marker that generates a marker signal, comprising:

a source generator;

a sensor panel assembly coupled to the source generator, the sensor panel assembly having a mass per unit area in a plane of a support panel of approximately 1.0 grams/cm$^2$ or less comprising:

a first coil layer having a plurality of source coils coupled to the source generator;

a second coil layer separate from the first coil layer and having a plurality of sensor coils, the sensor coils configured to receive the marker signal from the marker and to generate sensor signals based upon the marker signal; and a portable support panel laminated to the first and second coil layers with the source coils and the sensor coils in a substantially rigid, fixed position relative to each other;

a moveable module, wherein an articulating arm operably couples the sensor panel assembly to the moveable module; and a controller remote from the sensor panel assembly and coupled to the sensor coils to receive the sensor signals.

20. The system of claim 19 wherein the plurality of sensor coils are co-planar.

21. The system of claim 19 wherein the plurality of source coils are co-planar.

22. The system of claim 19 wherein the support panel includes a first stiffening spacer and a second stiffening spacer, and the first coil layer is laminated between the first and second stiffening spacers, and one of the first and second stiffening spacers is between the first and second coil layers.

23. The system of claim 19 wherein the support panel has a coil-cooling system configured to direct a flow of cooling fluid over the plurality of source coils.

24. The system of claim 19 wherein the sensor panel assembly has a mass per unit area in a plane of the support panel that averages approximately 0.3 grams/cm$^2$ or less.

25. An excitation panel assembly for use with a remote marker and a coolant source, comprising:

a plurality of source coils configured to generate a marker excitation field; and a moveable support panel coupled to the source coils, the support panel having a mass per unit area in a plane of the support panel of approximately 1.0 grams/cm$^2$ or less, the support panel having cooling channels integrally formed therein, the cooling channels being configured to remove heat from the source coils, wherein the movable support panel is operably connected to an articulating arm of a stand alone base module.

26. The assembly of claim 25, further comprising a coolant pump coupled to the support panel and in fluid communication with the cooling channels.

27. The assembly of claim 25 wherein the plurality of source coils define a first coil layer, and further comprising a second coil layer having an array of sensor coils, the first coil layer being spaced apart from the second coil layer.

28. The assembly of claim 25 wherein the plurality of source coils are substantially co-planar.

29. The assembly of claim 25 wherein the excitation panel assembly has a mass per unit area in a plane of the support panel that averages 0.3 grams/cm$^2$ or less.

30. A method of locating and irradiating a target in a patient with a radiation beam, comprising:

positioning a marker at a selected location relative to the target;

moving a sensor panel assembly to a position adjacent to the patient and between a radiation beam source and the patient, wherein moving the support panel includes articulating an arm operably coupling the sensor panel assembly to a base;

energizing the marker to generate a marker signal;

receiving the marker signal with the sensor panel assembly;

determining a location of the marker and the target in three-dimensional space; and irradiating the target with the radiation beam at the location of the target in three-dimensional space, the radiation beam passing through the sensor panel assembly while irradiating the target wherein the radiation beam undergoes beam attenuation of approximately 0.5% or less.

31. The method of claim 30 wherein irradiating the target includes increasing a skin dose of the radiation beam passing through the sensor panel assembly up to approximately 80% more than a skin dose of the radiation beam passing through air.

32. The method of claim 30 wherein the sensor panel assembly includes an optical target thereon, and the method further comprises locating the optical target and determining the location of the optical target relative to a determinable position of the radiation beam.

33. A method of generating a magnetic excitation field for energizing a remote leadless marker, comprising:

moving an excitation assembly to a position in a selected vicinity of the remote leadless marker, the excitation assembly having a plurality of source coils configured to generate a magnetic excitation field for excitation of the remote leadless marker, the excitation assembly having a support panel coupled to the source coils, the support panel having a coil-cooling system integrally formed therein and in fluid communication with the source coils, the support panel having a mass per unit area in a plane of the support panel of approximately 1.0 grams/cm$^2$ or less, wherein moving the excitation assembly includes articulating an arm operably interconnecting the support panel to a moveable base module;

generating the magnetic excitation field with the source coils;

energizing the marker assembly with the magnetic excitation field; and cooling the source coils with a flow of coolant from the coil-cooling system.

* * * * *